(12) United States Patent
Fujieda et al.

(10) Patent No.: US 6,977,105 B1
(45) Date of Patent: Dec. 20, 2005

(54) MULTILAYERED TUBE AND MEDICAL SUPPLY COMPRISING MULTILAYERED TUBE

(75) Inventors: Yukihiro Fujieda, Okayama (JP); Masayasu Ogushi, Ibaraki (JP); Motohiro Fukuda, Ibaraki (JP); Toshiyuki Zento, Ibaraki (JP); Koichi Wada, Ibaraki (JP); Toshiji Ichikawa, Oita (JP); Akira Ishida, Oita (JP)

(73) Assignees: Kuraray Co., Ltd., Kurashiki (JP); Kawasumi Laboratories, Inc., Tokyo (JP)

( * ) Notice: Subject to any disclaimer, the term of this patent is extended or adjusted under 35 U.S.C. 154(b) by 0 days.

(21) Appl. No.: 09/926,817

(22) PCT Filed: Sep. 22, 2000

(86) PCT No.: PCT/JP00/06493

§ 371 (c)(1),
(2), (4) Date: Dec. 21, 2001

(87) PCT Pub. No.: WO01/81808

PCT Pub. Date: Nov. 1, 2001

(30) Foreign Application Priority Data

Apr. 21, 2000 (JP) ................................ 12-120270

(51) Int. Cl.$^7$ ............................ B32B 1/08; F16L 11/04; F16L 11/20; A61M 25/00
(52) U.S. Cl. .................. 428/36.9; 428/36.91; 604/403; 604/408; 604/264; 138/137; 138/140
(58) Field of Search ............................ 428/36.91, 36.9; 604/403, 408, 264; 138/137, 140

(56) References Cited

U.S. PATENT DOCUMENTS 4,588,777 A * 5/1986 Hotta ........................... 525/93

(Continued)

FOREIGN PATENT DOCUMENTS

JP          4-132739          5/1992

(Continued)

OTHER PUBLICATIONS

Current translation of JP 09-254339.*

*Primary Examiner*—Harold Pyon
*Assistant Examiner*—Chris Bruenjes
(74) *Attorney, Agent, or Firm*—Oblon, Spivak, McClelland, Maier & Neustadt, P.C.

(57) ABSTRACT

A multi-layered tube composed of at least two layers, each formed from a different resin, e.g. resin (I) or resin (II). Resin (I) contains 5 to 40 mass % of a polypropylene resin and 95 to 60 mass % of at least one hydrogenated copolymer. Resin (II) contains 45 to 100 mass % of a polypropylene resin and 55 to 0 mass % of a hydrogenated copolymer. The multi-layered tubes may be used in the field of medicine and provide tubing which is excellent in transparency, flexibility and anti-kinking properties, and which is durable during sterilization procedures with high-pressure steam. The multilayer tubing may also be safely disposed of as it generates no toxic gases, such as dioxin, when incinerated. The multilayered tubing has excellent connectability and may be bonded to other tubing using hot solvent bonding or solvent adhesion. The multilayered tubing which is free from generation of any toxic gas when incinerated, and which is excellent in hot solvent bonding or solvent adhesion to other tube.

18 Claims, 3 Drawing Sheets

U.S. PATENT DOCUMENTS

| | | | | |
|---|---|---|---|---|
| 5,264,488 A | * | 11/1993 | Takeuchi et al. | 525/89 |
| 5,529,821 A | * | 6/1996 | Ishikawa et al. | 428/36.91 |
| 5,616,420 A | * | 4/1997 | Yamaoka et al. | 428/515 |
| 5,928,744 A | * | 7/1999 | Heilmann et al. | 428/36.6 |
| 5,936,037 A | * | 8/1999 | Tasaka | 525/92 B |
| 6,127,009 A | * | 10/2000 | Strassmann | 428/35.2 |
| 6,406,767 B1 | * | 6/2002 | Mueller | 428/36.91 |

FOREIGN PATENT DOCUMENTS

| | | |
|---|---|---|
| JP | 9-103493 | 4/1997 |
| JP | 9-123314 | 5/1997 |
| JP | 9-254339 | 9/1997 |

* cited by examiner

MULTILAYERED TUBE AND MEDICAL SUPPLY COMPRISING MULTILAYERED TUBE

CROSS-REFERENCE TO RELATED APPLICATIONS

This application is a national-stage filing under 35 U.S.C. §371 of PCT/JP00/06493, filed Sep. 22, 2000. This application also claims priority under 35, U.S.C. §119 to Japanese application 2000-120270, filed Apr. 21, 2000.

TECHNICAL FIELD

The present invention relates to a multi-layered tube and a medical device comprising the multi-layered tube. More specifically, the present invention relates to a multi-layered tube for medical use which is excellent in flexibility, transparency, anti-kinking properties and restoration capability after occlusion, which also has durability against high-pressure steam sterilization, and which is excellent in connectability to other tube having a different diameter, a connecter, a joint, and the like.

The multi-layered tube of the present invention is suitable for use as a component for medical devices such as a blood circuit line, a blood bag, a medicinal fluid bag, a blood transfusion/infusion set, a catheter, and the like.

TECHNICAL BACKGROUND

Polyvinyl chloride has been and is widely used not only in the fields of industries and household articles but also in the fields of medical treatment and welfare. Particularly, most of disposable medical devices are produced from polyvinyl chloride. Since, however, soft polyvinyl chloride contains a relatively large amount of plasticizers such as dioctyl phthalate (DOP), etc., the problem of elution of the plasticizer into blood or a medicinal solution is pointed out from the viewpoint of safety of medical devices.

On the other hand, from the viewpoint of infection prevention, steps are taken forward to dispose medical devices, and it is required by the law to dispose of used medical devices by incineration. It is said that polyvinyl chloride generates almost no toxic chlorine-containing substances such as dioxin since it is converted finally to carbon dioxide, water and hydrogen chloride when combusted at a temperature of approximately 850 to 900° C. with feeding sufficient oxygen. In reality, however, the problem of environmental pollution with dioxin or other toxic chlorine-containing substance frequently takes place for reasons that there are not sufficient incinerators that can withstand said high temperatures, that there are small-sized incinerators of which the incineration capacity is insufficient and that there are few plants for dioxin disposal.

Studies are recently being made for changing the material in the fields of medical devices, industries and a household devices from the soft vinyl chloride to other materials.

As a polyvinyl-chloride-free material for medical tubes, studies are made on polyethylene (PE), polypropylene (PP), an ethylene-vinyl acetate copolymer (EVAC), polyethyl methacrylate (PEMA), a styrene-butadiene block copolymer, a hydrogenation product of a styrene-isoprene copolymer (styrene-based thermoplastic elastomer), and the like.

For example, as a resin composition that gives a molded article excellent in flexibility and suitable for medical use, JP-A-4-158868 (Literature 1), JP-A-4-159344 (Literature 2) and JP-A-8-131537 (Literature 3) propose a resin composition (styrene-based thermoplastic elastomer) containing an olefin resin, a hydrogenation product of a styrene-butadiene block copolymer (styrene-based thermoplastic elastomer) and a hydrogenation product of a styrene-isoprene block copolymer.

Further, JP-A-9-103493 (Literature 4) and JP-A-123314 (Literature 5) disclose a multi-layered tube formed of a substrate layer and an adhesive layer in which the adhesive layer is made of a material that is not dimensionally stable at an autoclave sterilization temperature (121° C.) or higher and tends to flow under a connection pressure with other tube having a different diameter during autoclave sterilization at 121° C.

(1) In principle, however, a tube made of the above PE, EVAC or PEMA has flexibility but has a problem that the tube, when made of a single material, is liable to undergo kinking (which refers to a phenomenon that the tube bends or is twisted to come into the state where internal surfaces of the tube become stuck or adhered together).

(2) While the above styrene-based thermoplastic elastomer as a single material or a composition containing 60 mass % thereof or more has flexibility, they come to have sticking nature on the surface when sterilized with high-pressure steam (autoclave sterilization), so that they are not suitable for use as a material to form a surface that will contact blood. Further, they have a problem that the internal surface of the tube undergoes self-sticking (self-adhesion) when the tube is clamped with a forceps and the tube shows poor restoration capability when it was released from clamping after occlusion.

(3) Further, a tube made of the above PP as a single material or a composition containing at least 40 mass % thereof is too rigid and not flexible enough to prevent 1=4 kinking.

The resin composition described in the above Literatures 1 to 3 has characteristic features that it gives a molded article excellent in flexibility and it does not involve the generation of an toxic gas such as dioxin when the molded article is incinerated. However, ① when emphasis is placed on flexibility, a single-layered tube made of the above resin composition has a higher proportion of the styrene-based thermoplastic elastomer, and the tube suffers problems that are not negligible, that is, it has poor heat resistance problem that the cross section of the tube sterilized in an autoclave is deformed or one tube is fused with another or a problem that the tube has poor restoration capability when released from clamping with a forceps after occlusion with it. ② When emphasis is placed on heat resistance and restoration capability after occlusion, the proportion of the styrene-based thermoplastic elastomer comes to be smaller, and the tube becomes less flexible and is not at all satisfactory as a medical tube. It is therefore desired to improve the tube in these points.

In a multi-layered tube, hot melt bonding or solvent bonding is the most preferred in view of reliable connection. In the multi-layered tube described in Literature 4 or 5, the adhesive layer is made of a material that is not dimensionally stable at an autoclave sterilization temperature (121° C.) or higher and tends to flow under a connection pressure with other tube having a different diameter during autoclave sterilization at 121° C., and the tube is connected to the other tube by "press fitting" between these tubes. These tubes are therefore intimately connected by adherence, so that one tube easily comes off from the other under small force. Further, since tackiness is caused under heat by the autoclave sterilization, fitted portions may come apart one from the other during the sterilization or at a step prior thereto, and it is considered that such a material is not suitable for producing medical devices.

As performances required for medical tube that can be sterilized with high-pressure steam, preferably, the tube satisfies the following conditions:

That is, (a) the tube is to have proper flexibility without keeping on kinking or bending when bent, (b) the tube is to show no stickiness (tackiness) on the surface and is to be free from any change in form and dimensions when sterilized with high-pressure steam, and (c) the tube permits hot melt bonding or solvent bonding when connected to other tube having a different diameter or an injection-molded article.

As described above, it is an object of the present invention to provide a multi-layered tube which is excellent in transparency, flexibility, anti-kinking properties, restoration capability after occlusion and heat resistance and which elutes no plasticizer and generates no toxic gas when incinerated, and to provide a medical device comprising said multi-layered tube.

DISCLOSURE OF THE INVENTION

The present inventors have made diligent studies from the above viewpoints and as a result have found that the above object can be achieved by providing a multi-layered tube having layers having different compositions comprising a polypropylene resin and at least one copolymer selected from a hydrogenated block copolymer of a polymer block from a vinyl aromatic compound and an isoprene and/or butadiene block and a hydrogenation product of a copolymer from a vinyl aromatic compound and butadiene, and a medical device comprising the above multi-layered tube. The present invention has been accordingly made.

That is, according to the present invention, there are provided the following inventions [1] and [2]. [1] A multi-layered tube composed of at least two layers, wherein at least one layer of said layers is a layer (I) made of a resin composition comprising 5 to 40 mass % of a polypropylene resin (a), and 95 to 60 mass % of at least one copolymer (b) selected from the group consisting of a hydrogenated block copolymer (b1) obtained by hydrogenation of a block copolymer formed of a polymer block (A) from a vinyl aromatic compound and an isoprene polymer block (B), a hydrogenated block copolymer (b2) obtained by hydrogenating a block copolymer formed of a polymer block (A) from a vinyl aromatic compound and a polymer block (C) from isoprene and butadiene, a hydrogenated block copolymer (b3) obtained by hydrogenating a block copolymer formed of a polymer block (A) from a vinyl aromatic compound and a butadiene polymer block (D), and a hydrogenated copolymer (b4) obtained by hydrogenating a copolymer of a vinyl aromatic compound and butadiene, and at least one layer of the remaining layer or layers is a layer (II) formed of a resin composition comprising 45 to 100 mass % of a polypropylene resin (a) and 55 to 0 mass % of the above copolymer (b), and further wherein said layer (I) forms one layer of an inner layer and an outer layer and said layer (II) forms the other layer, or said layer (I) forms an intermediate layer and the layer (II) forms the inner layer and the outer layer.

[2] A medical device comprising said multi-layered tube and other member to which said multi-layered tube is connected.

BRIEF DESCRIPTION OF DRAWINGS

In the drawings, 1 indicates a multi-layered tube, 3 indicates an inner layer, 5 indicates an outer layer, 7 indicates an intermediate layer, 50 indicates a connection member, 55 indicates an internal surface of the connection member, 57 indicates an external surface of the connection member, I indicates a layer (I), and II indicates a layer (II).

PREFERRED EMBODIMENTS OF THE INVENTION

The present invention will be explained in detail hereinafter.

The polypropylene resin (a) for constituting the multi-layered tube of the present invention can be selected from known polypropylene resins, and it may be any one of homo polypropylene, random polypropylene and block polypropylene. The polypropylene resins (a) may be used alone or in combination. Basically, when measured according to ASTMD-1238 at 230° C. under a load of 2,160 g, the polypropylene resin (a) preferably has a melt flow rate (MFR) in the range of from 0.1 to 500, more preferably in the range of from 0.1 to 200.

As a polypropylene resin for the layer (I), the above polypropylene preferably has a bending flexural modulus of 200 to 400 MPa (crystallinity of 30 to 40% and a molecular weight of 50,000 to 200,000). As a polypropylene resin for the layer (II), the above polypropylene preferably has a bending flexural modulus of 500 to 900 MPa (crystallinity of at least 50% and a molecular weight of 100,000 to 500,000).

In principle, the layer (I) is a layer that forms a component constituting a substrate of the multi-layered tube, and the layer (II) is a layer that works as a connection layer when the multi-layered tube is connected to other part to form a medical device.

When the polypropylene resin to be incorporated into the layer (I) has a bending flexural modulus in the above range, the tube can be imparted with flexibility and anti-kinking properties. When the flexural modulus is less than 200 MPa, the tube is too soft and exhibits no nerve (stiffness). When it exceeds 400 MPa, undesirably, the tube is liable to keep on kinking and bending when bent.

When the polypropylene resin to be incorporated into the layer (II) has a bending flexural modulus in the above range, the layer (II) can be imparted with a nerve (stiffness) so that flowing of the layer (II) during sterilization with high-pressure steam can be prevented.

The copolymer (b) used in the present invention is a hydrogenating block copolymer ((b1)–(b3)) obtained by hydrogenating a copolymer formed of a polymer block (A) from a vinyl aromatic compound and a polymer block ((B)–(D)) from an isoprene and/or butadiene, or a hydrogenated copolymer (b4) obtained by hydrogenating a copolymer of a vinyl aromatic compound and butadiene.

In the hydrogenated block copolymers ((b1)–(b3)), the vinyl aromatic compound is preferably styrene, and the hydrogenated block copolymers ((b1)–(b3)) are desirably a hydrogenated product (b1) of a styrene-isoprene-styrene copolymer, a hydrogenated product (b2) of a styrene-isoprene/butadiene-styrene copolymer, a hydrogenated product (b3) of a styrene-butadiene-styrene copolymer, and the like.

The hydrogenated copolymer (b4) is a hydrogenated copolymer obtained by hydrogenating a copolymer of a vinyl aromatic compound and butadiene as described above. Preferably, the vinyl aromatic compound is styrene, and the hydrogenated copolymer (b4) is a hydrogenated styrene-butadiene-rubber. It is particularly desirable to use a type of the hydrogenated copolymer (b4) that is ultra-finely dispersible in polypropylene.

As a vinyl aromatic compound for the copolymer (b), such vinyl aromatic compounds as described later can be used besides the styrene.

In the present invention, the layer (I) is a layer formed of a resin composition containing 5 to 40 mass %, preferably 15 to 35 mass %, more preferably 20 to 30 mass % of the polypropylene resin (a) and 95 to 60 mass %, preferably 85 to 65 mass %, more preferably 80 to 70 mass % of the copolymer (b).

Basically, the multi-layered tube of the present invention has the layer (I) as a substrate layer, so that the multi-layered tube can be imparted with flexibility and anti-kinking properties. That is, when the content of the copolymer (b) exceeds 95 mass %, the tube is too soft and has no nerve, and when the tube is closed with a medical tube forceps for 15 hours and then released from the forceps, the tube does not easily gain a through passage inside the tube within 3 seconds. Further, when the tube is subjected to heat-treatment such as autoclave sterilization (121° C., 20 minutes), the cross section of the tube is easily deformed. The tube is therefore poor in restoration capability after occlusion and heat resistance. Further, when the above content is less than 60 mass %, the resin composition has a high elastic modulus, and the tube has low flexibility, so that the tube is undesirably liable to keep on kinking or bending when bent.

Further, in the present invention, basically, the layer (II) to form a connection layer is a layer formed of a a resin composition containing 45 to 100 mass % of the polypropylene resin (a) and 55 to 0 mass % of the copolymer (b).

The composition for the layer (II) can be determined to be optimum depending upon the object. That is, when the layer (II) is used as an outer layer, the content of the polypropylene resin (a) is at least 45 mass %. In this case, sticking of one tube to another during sterilization with high-pressure steam or sticking of the tube to a packing material can be prevented. When the multi-layered tube of the present invention is to be connected to other tube having a different diameter or to a part such as an injection-molded article with a solvent bonding or an adhesive bonding or by hot melt bonding, preferably, the content of the polypropylene resin (a) in the layer (II) to constitute an connection layer (outer layer and/or inner layer) is determined to be 70 mass % or less in view of adhesion capability.

When the layer (II) is used as an inner layer, the content of the polypropylene resin (a) is determined to be at least 70 mass %. In this case, when the medical forceps is removed after the tube is closed with the forceps, the tube can restore its original form in a short period of time, and that the passage for a fluid can be secured. Further, when the multi-layered tube of the present invention is used in a way where it is being contact with blood like in a blood circuit or a blood tube, preferably, the content of the polypropylene resin (a) in the layer (II) that comes to be in contact with blood is at least 70 mass %, from the viewpoint of affinity to blood such as anti-coagulation of blood. As c) described above, the optimum composition for the layer (II) can be determined as required depending upon use.

In the present invention, the copolymer (b) is preferably the following hydrogenated block copolymer ((b1)–(b3)) or a hydrogenated polymer (b4).

In the copolymer (b), the content of the vinyl aromatic compound is preferably 10 to 40 mass %. When the content of the vinyl aromatic compound is less than 10 mass %, the tube sometimes has insufficient mechanical strength. When it exceeds 40 mass %, the composition has a high melt viscosity, so that the vinyl aromatic compound is poorly mixed with the polypropylene resin (a), which may impose limitations on molding.

In the isoprene polymer block (B) of the hydrogenated block copolymer (b1), preferably, the content of 1,2-bonds and 3,4-bonds (to be sometimes referred to as "vinyl bond content" hereinafter) is 10 to 75 mass %. When the vinyl bond content is too small, such a content is insufficient for transparency. When it is too large, the glass transition temperature of the resin composition comes to be too high, and the flexibility of a molded article from the resin composition is liable to be impaired. When the hydrogenation ratio of carbon—carbon double bonds in the copolymer (b1) is too small, the multi-layered tube tends to be poor in weatherability and heat resistance, so that the above hydrogenation ratio is preferably at least 70%. The reference to transparency is made above, since when the multi-layered tube of the present invention is used as a component of a medical device, it is desirable that the multi-layered tube has excellent transparency.

As the hydrogenated block copolymer (b2), it is preferred for the same reasons to use a hydrogenated block copolymer having an isoprene-butadiene copolymer block (C) having a 1,2-bond and 3,4-bond content of 20 to 85% and having carbon—carbon double bonds at least 70% of which are hydrogenated.

As the hydrogenated block copolymer (b3), it is also preferred for the same reasons to use a hydrogenated block copolymer having a butadiene polymer block (D) having a 1,2-bond content of at least 30% and having carbon—carbon double bonds 70% of which are hydrogenated.

In the copolymer (b), examples of the vinyl aromatic compound include styrene, α-methylstyrene, 1-vinylnaphthalene, 3-methylstyrene, 4-propylstyrene, 4-cyclohexylstyrene, 4-dodecylstyrene, 2-ethyl-4-benzylstyrene and 4-(phenylbutyl) styrene. Of these, styrene is particularly preferred.

Although not specially limited, the number average molecular weight of the polymer block (A) formed from the above vinyl aromatic compound is preferably in the range of from 2,500 to 20,000.

Although not specially limited, the number average molecular weight of each of the polymer blocks (B), (C) and (D) is preferably in the range of from 10,000 to 200,000. While the form of a polymer from isoprene and butadiene in the polymer block (C) is not specially limited, it may be any form of random, block and tapered forms.

In the copolymer (b), the form of bonding of each polymer block ((B), (C) or (D)) is not specially limited, and it may be linear, branched or any combination of these.

Specific examples of the molecular structure of the copolymer (b) include $P(QP)_n$ and $(PQ)_n$, in which P is the polymer block (A), Q is a polymer block (B), (C) or (D) and n is an integer of 1 or greater.

As the copolymer (b), further, there can be used a copolymer having a star-shaped molecular structure obtained in the presence of divinylbenzene, a tin compound or a silane compound as a coupling agent (e.g., a polymer represented by $[(PQ)_m X]$ in which P and Q are as defined above, m is an integer of 2 or greater and X is a residue of the coupling agent.

As the copolymer (b), copolymers having the above various molecular structures may be used alone, or two or more copolymers having the above various molecular structures such as a mixture of triblock type and diblock type copolymers may be used. The number average molecular weight of the above copolymer (b) is preferably in the range of from 30,000 to 300,000.

The method for producing the copolymer (b) can be selected from known production methods, and for example, there can be employed a method of hydrogenating a block copolymer obtained by any one of the following methods ($\alpha$) to ($\gamma$), that is, ($\alpha$) a method in which a vinyl aromatic compound is polymerized in the presence of an alkyllithium compound as an initiator, and then a conjugated diene compound (isoprene, butadiene) and a vinyl aromatic compound are consecutively polymerized, ($\beta$) a method in which a vinyl aromatic compound is polymerized, then a conjugated diene compound is polymerized, and the coupling of the resultant block copolymers is carried out in the presence of a coupling agent, and ($\gamma$) a method in which a conjugated diene compound is polymerized in the presence of a dilithium compound as an initiator and then a vinyl aromatic compound is consecutively polymerized.

In the above method, the alkyllithium compound as an initiator is selected from compounds whose alkyl group has 1 to 10 carbon atoms, and of these, methyllithium, ethyllithium, pentyllithium, n-butyllithium, s-butyllithium and t-butyllithium are preferred. Examples of the coupling agent for coupling the block copolymer include halogen compounds such as dichloromethane, dibromomethane, dichloroethane, dibromoethane, dibromobenzene and tin tetrachloride; ester compounds such as phenyl benzoate and ethyl acetate; divinylbenzene, and various silane compounds. Further, examples of the dilithium compound as an initiator include naphthalenedilithium and dilithiohexylbenzene.

The amount of the above initiator or the coupling agent is determined as required depending upon the molecular weight of a desired block copolymer. Per 100 parts by weight of all the entire monomers used for the polymerization, generally, the amount of the initiator is in the range of from 0.01 to 0.2 part by weight, and the amount of the coupling agent is in the range of from 0.04 to 0.8 part by weight.

The vinyl bond content in each of the polymer blocks N (B) to (D) can be controlled by the use of a Lewis base as a cocatalyst in the polymerization. Examples of the above Lewis base include ethers such as dimethyl ether, diethyl ether and tetrahydrofuran; glycol ethers such as ethylene glycol dimethyl ether and diethylene glycol dimethyl ether; and amine-containing compounds such as triethylamine, N,N,N',N'-tetramethylethylenediamine (to be abbreviated as "TMDA" hereinafter) and N-methylmorpholine. The Lewis base is used in such an amount that the molar amount of the Lewis base per mole of the lithium atom in the polymerization initiator is in the range of from 0.1 to 1,000 mol.

In the polymerization, it is preferred to use an organic solvent inert to the polymerization initiator as a solvent. The above solvent is preferably selected from aliphatic hydrocarbons having 6 to 12 carbon atoms such as hexane and heptane; alicyclic hydrocarbons such as cyclohexane and methylcyclohexane; or aromatic hydrocarbons such as benzene. In any one of the above polymerization methods ($\alpha$) to ($\gamma$), the polymerization is generally carried out at a temperature range of from 0 to 80° C., and the reaction time period is generally 0.5 to 50 hours.

Then, the block copolymer obtained by the above method is converted to the hydrogenated block copolymer (b1), (b2) or (b3), for example, by a known method, such as a method in which hydrogen in a molecular state is reacted with the block copolymer in the presence of a known hydrogenation catalyst in a state where the block copolymer is dissolved in a solvent inert to the reaction. The above hydrogenation catalyst is selected from heterogeneous catalysts composed of a metal such as Raney nickel, Pt, Pd, Ru, Rh or Ni supported on a carrier such as carbon, alumina or diatomaceous earth to support; Ziegler catalysts formed of combinations of organometalic compounds of metals belonging to the group VIII of the periodic table such as nickel and cobalt with organic aluminum compounds or organic lithium compounds such as triethylaluminum and triisobutylaluminum; or metallocene catalysts formed of combinations of bis (cyclopentadienyl) in compounds of transition metals such as titanium, zirconium and hafnium with an organometalic compound of lithium, sodium, potassium, aluminum, zinc or magnesium.

The hydrogenation is generally carried out under a hydrogen pressure in the range of from normal pressure to 20 MPa at a reaction temperature in the range of from room temperature to 250° C. The reaction time period is generally 0.1 to 100 hours. The copolymer (b) obtained by the above hydrogenation is recovered (i) by coagulating the reaction mixture in methanol, or the like and then heating the coagulated reaction mixture or drying it under reduced pressure, or (ii) by carrying out so called steam stripping in which the reaction solution is poured into boiling water and the solvent is azeotropically removed, and heating the reaction product or drying it under reduced pressure.

In the multi-layered tube of the present invention, the layer (I) preferably has an elastic modulus (elastic modulus of the layer per se) of 30 MPa or less at 25° C. Further, each of the layer (I) and the layer (II) preferably has a haze of 25% or less at the thickness of 1 mm. Further, preferably, the multi-layered tube of the present invention can form an arc having a radius of 20 mm without kinking.

The multi-layered tube of the present invention may be used as it is. Practically and preferably, however, the layer(s) (II) forming the outer surface and/or the inner surface of the multi-layered tube is/are used as connection layer(s), and other tube having a different diameter, a connector or a joint is connected thereto before use. The above connection is attained by solvent bonding or hot melt bonding, or may be attained by bonding with an adhesive.

Further, in the multi-layered tube of the present invention, preferably, the shear peel strength of the stuck portion (adhered portion) of outermost layers of the multi-layered tubes after autoclave sterilization at 121° C. for 20 minutes is 35 N or lower, and the 180° peel strength of an stuck portion of the outermost layer and a polyolefin such as polypropylene forming the innermost layer after the sterilization is 5 N or lower. The term "180° peel strength" in the present invention refers to a strength measured by a test method defined in JIS K6854.

The multi-layered tube of the present invention is suitable as a medical tube for an extracorporeal circulation circuit, and, preferably, the multi-layered tube can form a through passage inside it within 3 seconds when it is closed with a medical tube forceps for 15 hours and then released from the forceps.

Each resin composition for constituting the multi-layered tube of the present invention may contain additives such as an antioxidant, an UV absorbent, a light stabilizer, a colorant, a crystal nucleating agent, etc., in such amounts that the properties of the multi-layered tube are not impaired. Generally, the amount of these additives per 100 parts by mass are in the range of from 0.01 to 5 part by mass.

Each resin composition for constituting the multi-layered tube may contain other polymers such as hydrogenated polyisoprene, hydrogenated polybutadiene, a hydrogenated styrene-isoprene random copolymer, butyl rubber, polyisobytylene, polybutene, ethylene-propylene rubber, an ethylene-α-olefin copolymer, an ethylene-vinyl acetate copolymer, an ethylene-methacrylic acid copolymer, an ethylene-acrylic acid coplymer, ionomers of these, an ethylene-ethyl acrylate copolymer, an ethylene-methyl methacrylate copolymer, an ethylene-ethyl methacrylate copolymer, atactic polypropylene, and the like, in such amounts that the gist of the present invention is not impaired. The above resin compositions may be crosslinked by a general crosslinking method using a peroxide, etc., before use.

The resin compositions for constituting the multi-layered tube of the present invention may be prepared by kneading the polypropylene resin (a), the copolymer (b) and optionally the above additive(s) with a kneading machine such as a single-screw extruder, a twin-screw extruder, a kneader, a Banbury mixer, a roll, or the like. The thus-prepared resin compositions are formed into the multi-layered tube by co-extrusion or coating.

The multi-layered tube of the present invention is excellent in flexibility, transparency, anti-kinking properties, restoration capability after occlusion and heat resistance. That is, specifically, ① when an optical bubble detector is used, 1 mL single bubble is detected at a flow rate of 300 mL/minute, ② each of the compositions forming the layers has a haze of 25% or less at the thickness of 1 mm, ③ when the multi-layered tube is formed into an arc having a radius of 20 mm, it is not bent, ④ when the multi-layered tube is closed with a medical tube forceps for 15 hours and then released from the forceps, the tube forms a through passage inside within 3 seconds, and ⑤ after the multi-layered tube is sterilized in an autoclave (121° C., 20 minutes), the shear peel strength of the stuck portion of the outermost layers of the multi-layered tubes is 35 N or lower, and the 180° peel strength of an stuck portion of the outermost layer of the tube and a sterilization bag having the innermost layer formed of polypropylene is 5 N or lower.

Figure 1A:
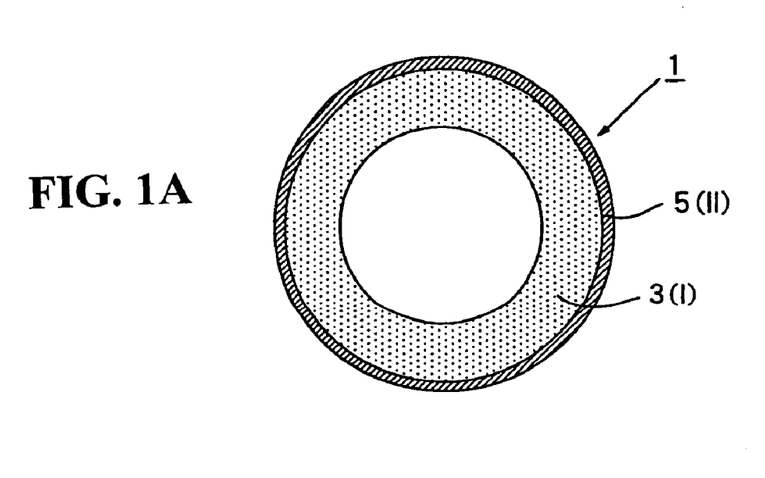
FIGS. 1A–1C shows cross-sectional views of multi-layered tubes 1 of the present invention.
Figure 1B:
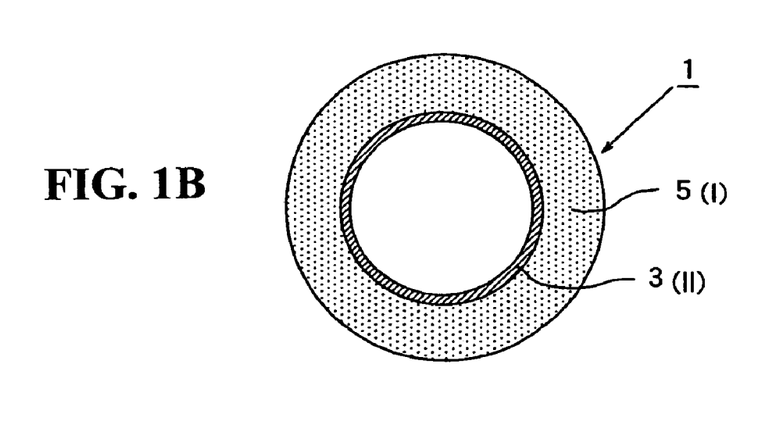
Figure 1C:
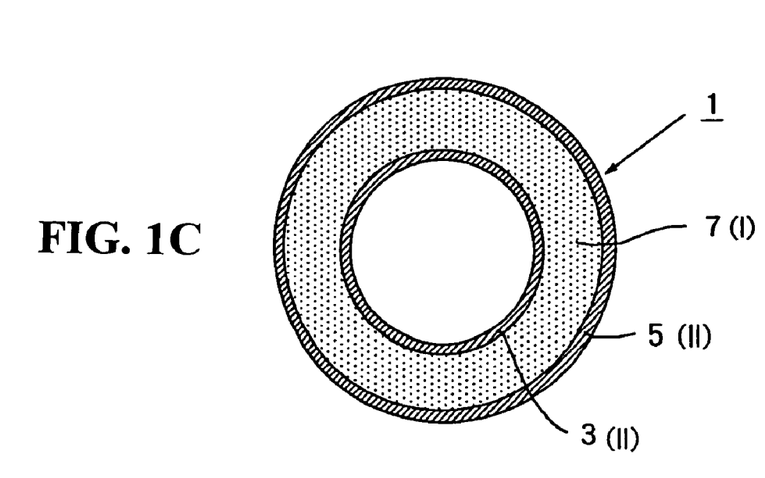
Figure 2:
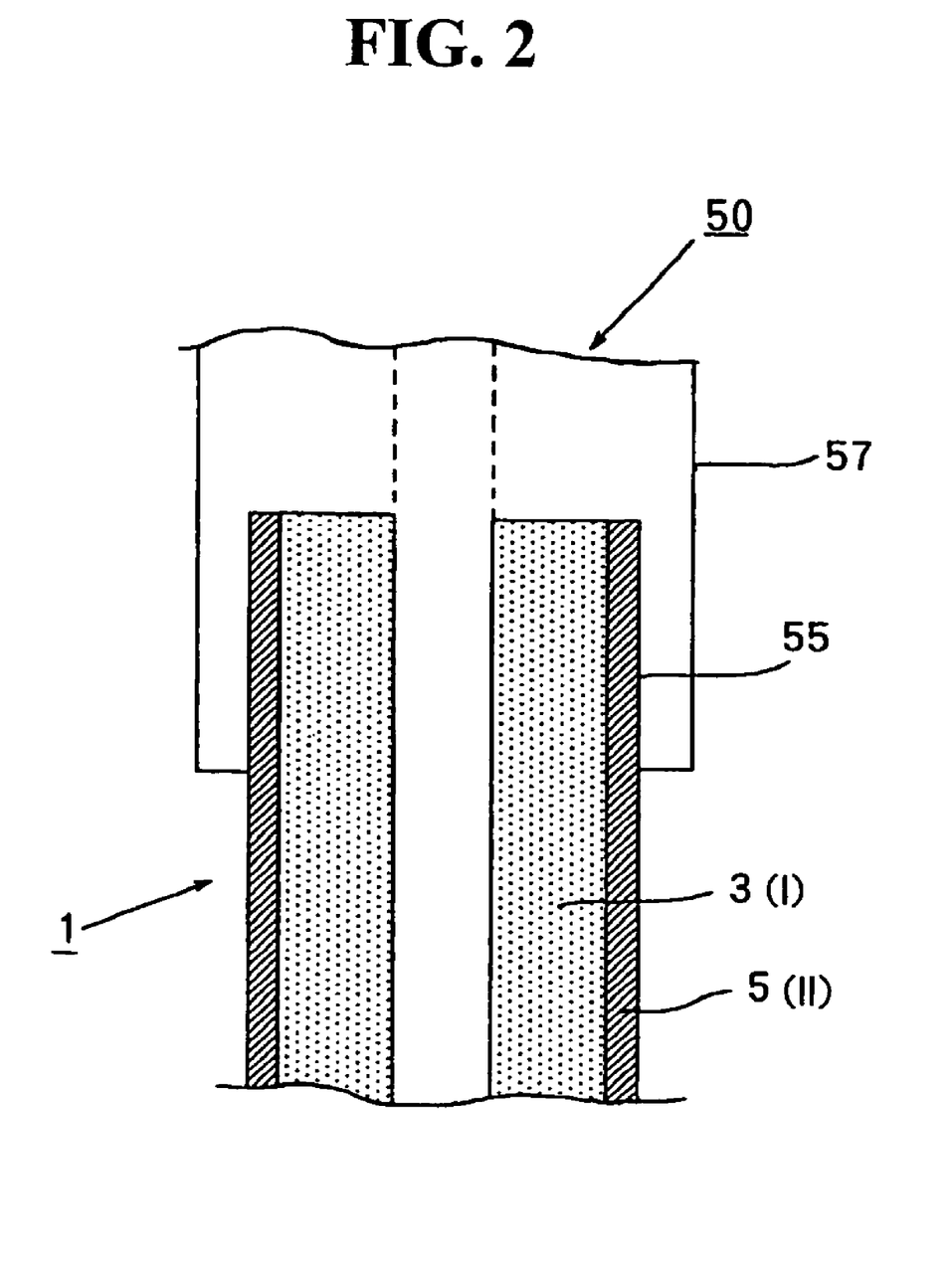
FIG. 2 is a partially enlarged longitudinal sectional view of a medical device comprising the multi-layered tube of the present invention connected to other connection member having a different diameter.
Figure 3:
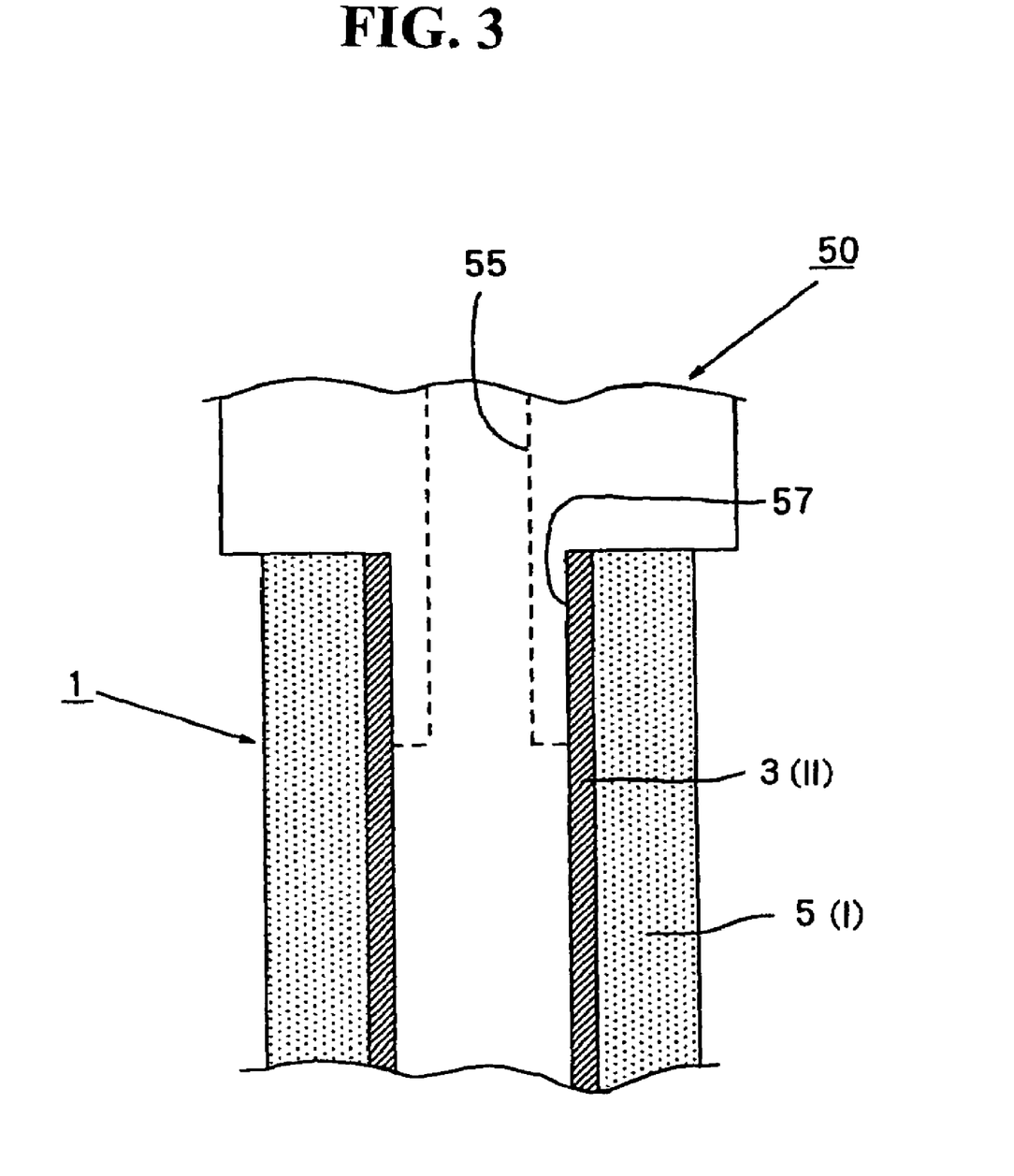
FIG. 3 is a partially enlarged longitudinal sectional view of a medical device comprising the multi-layered tube of the present invention connected to other connection member having a different diameter.

One example of the embodiment of the present invention will be explained with reference to attached drawings hereinafter. FIG. 1A–1C shows cross-sectional views of multi-layered tubes of the present invention. FIGS. 2 and 3 are partially enlarged longitudinal sectional views of medical device comprising the multi-layered tube of the present invention connected to other connection members such as other tube having a different diameter and an injection-molded article. In addition, the injection-molded article in the present invention refers to a tubular member connectable to the multi-layered tube of the present invention and includes, for example, a connector and a joint.

In FIG. 1A, a multi-layered tube 1 is a dual layered tube formed of the layer (I) forming an inner layer 3 and the layer (II) forming an outer layer 5. In FIG. 1B, a multi-layered tube 1 is a dual layered tube formed of the layer (I) forming an outer layer 5 and the layer (II) forming an inner layer 3. In FIG. 1C, further, a multi-layered tube 1 is a three-layered tube formed of the layer (I) forming an intermediate layer 7 and the layers (II) forming an inner layer 3 and an outer layer 5.

FIG. 2 shows a state in which the dual layered tube 1 shown in FIG. 1A is connected to a connection member 50 such as other tube having a different diameter or an injection-molded article, and the layer (II) forming the outer layer 5 and an inner wall surface 55 of the connection member 50 can be connected to each other. The term "connection" means connection with a solvent bonding or hot melt bonding as already described. The adhesion by hot melt bonding includes application of a hot melt bonding using electric heat, high-frequency hot melt bonding and hot melt bonding by heating with hot air. However, the bonding shall not be limited thereto, and other hot melt bonding may be employed. FIG. 3 also shows a state where the dual tube shown in FIG. 1B and the connection member 50 are connected to each other, and the layer (II) forming the inner layer 3 and an outer wall surface 57 of the connection member 50 are connected to each other similarly with a solvent bonding or by hot melt bonding.

In the dual layered tube, the thickness ratio of the layer (I) and the layer (II), layer (I)/layer (II), is preferably 940–980/60–20. That is because the entire tube is imparted with flexibility and anti-kinking properties by allowing the layer (I) to have a sufficient thickness as compared with the layer (II). That is, when the thickness ratio of the layer (I) is less than 940 (when the thickness ratio of the layer (II) exceeds 60), the wall thickness of the tube is small and kinking is liable to occur. When the thickness ratio of the layer (I) exceeds 980 (when the thickness ratio of the layer (II) is less than 20), the tube wall thickness is extremely large, and the rigidity is too large, so that the tube is liable to have decreased flexibility. Further, the thickness of the layer (II) is too small, and the tube tends to be no longer suitable for application of solvent bonding or hot melt bonding.

In the three-layered tube, the thickness ratio of the layer (I) and the layers (II), layer (II)/layer (I)/layer (II), is preferably 20–30/940–960/20–30. When the thickness ratio of the layer (I) is less than 940 (when the thickness ratio of the layer(s) (II) exceeds 30), the tube wall thickness is too small, and kinking is liable to occur. When the thickness ratio of the layer(s) (II) is less than 20 (when the thickness ratio of the layer (I) exceeds 960), the thickness of the layer (II) is too small, so that it is difficult to apply solvent bonding or hot melt bonding.

When the multi-layered tube of the present invention as a component is connected to a member such as other tube having a different diameter or an injection-molded article as described above, it can suitably form medical devices such as a blood circuit, a blood bag, a catheter, or the like.

The multi-layered tube of the present invention makes the best use of the above properties and can be used in an extracorporeal circulation circuit such as a blood circuit for artificial kidney dialysis, a blood circuit for blood plasma exchange, a circuit for ascites treatment systems by filtration, concentration and infusion, or the like. Further, in addition to the above extracorporeal circulation circuit, the multi-layered tube of the present invention can be used, for example, in various medical devices such as a blood tube, an infusion tube, a catheter, a balloon catheter, etc., industrial uses such as a hose, fields in agricultures, forestry and fisheries and the field of household articles, where excellent flexibility and transparency are required.

EXAMPLES

The present invention will be explained with reference to Examples hereinafter, in which "%" stands for "mass %" unless otherwise specified.

In the following Referential Examples 1 and 2, Examples 1 to 5 and Comparative Example 1, multi-layered tubes were evaluated for sticking of tubes to each other during sterilization, anti-kinking properties and adhesion by the following methods.

(Sticking During Sterilization)

Tubes were fixed with a paper tape so as to intimately adhere to each other, and the tubes were sterilized in an autoclave at 121° C. for 20 minutes and then measured for a shear peel resistance.

(Kinking Occurrence Radius)

Both ends of a 20 cm long tube were fixed to tools, the distance between the tools was gradually decreased, dimensions were taken when the tube was bent, and a radius of curvature was calculated.

(Solvent Bonding Properties)

A tube that had an internal diameter of 6.8 mm and was prepared from the same composition as that of an adhesive layer was used for bonding with THF, and after 24 hours, the tube was measured for a tensile strength.

Referential Example 1

Determination of Amount Ratio for Layer (II)

For the layer (II), polypropylene (F327) and a styrene-isoprene-styrene hydrogenated block copolymer (HVS-3) were mixed in amount ratios shown in Table 1 to prepare a tube having an outer diameter of 6.8 mm, and the tube was measured for sticking strength during sterilization and strength of solvent bonding. Table 1 shows the results.

TABLE 1

| Amount ratio of PP (a)/Copolymer (b) | Sticking strength of one tube to another | Strength of bonding to tube having a different diameter |
|---|---|---|
| 100/0 | No sticking | 6 N |
| 70/30 | Less than 10 N | 90 N |
| 50/50 | 34 N | 97 N |
| 40/60 | 36 N | 105 N |

According to the results in Table 1, when the amount ratio of the polypropylene resin (a), in the amount ratio of the polypropylene resin (a) and the copolymer (b), is 70 or less (when the amount ratio of the copolymer (b) is 30 or greater), the bonding strength of the tube to the tube having a different diameter is good. However, when the amount ratio of the polypropylene resin (a) is 40 or less (when the amount ratio of the copolymer (b) is 60 or greater), undesirably, the sticking strength of the tubes to each other comes to be 36 N or more.

When the amount ratio of the polypropylene resin (a) exceeds 70 (when the amount ratio of the copolymer (b) is less than 30), the sticking of the tubes to each other is desirably less than 10 N. Undesirably, however, the bonding strength to the tube having a different diameter is less than 90 N.

It is therefore seen that the polypropylene resin (a)/copolymer (b) amount ratio is preferably determined to be 70/30 to 45/55 for preventing the sticking of tubes to one another during sterilization and maintaining the strength of solvent bonding to a tube having a different diameter.

Examples 1–5 and Comparative Example 1

A commercially available polypropylene [F327 (trade name), supplied by Grand Polymer Inc., flexural modulus (JIS K7203): 780 MPa] was used as a polypropylene resin (a), and a commercially available hydrogenated styrene-ethylene-butylene-styrene block copolymer [Kraton G G1652 (trade name), supplied by Shell Chemical Co.], a hydrogenated isoprene copolymer [Hybrar HVS-3 (trade name), supplied by Kuraray Ltd.] or a hydrogenated styrene-butadiene rubber [DYNARON 1320P (trade name), supplied by JSR] was used as a copolymer (b).

The above polypropylene resin (a) and the copolymer (b) were mixed in a mixing ratio shown in Table 2, to prepare a resin composition.

The above resin compositions were co-extruded to form a three-layered tube having a layer (II) (outer layer)/layer (I) (intermediate layer)/layer (II) (inner layer) structure.

The three-layered tube has a size of 7 mm as an outer diameter and 1 mm as a wall thickness, and the thickness ratio of the layer (I) and the layers (II) were as shown in Table 2.

The above multi-layered tube was measured for stickiness of tubes to each other during sterilization, anti-kinking properties and bonding properties, and Table 2 shows the results.

As is clearly shown in Table 2, the three-layered tubes of Examples 1 to 5 according to the present invention nearly satisfy the formerly described performances (a) to (c) which a medical tube is required to have. In contrast, when the amount ratio of the polypropylene is decreased and the amount ratio of the copolymer (b) is increased in the composition for the layers (II) like Comparative Example 1, the sticking during sterilization increases.

In Referential Examples 2 to 4, Examples 6 to 16 and Comparative Examples 2 and 3, polymers were measured for styrene contents, number average molecular weights, vinyl bond contents and hydrogenation ratios, molded articles from resin compositions were measured for flexibility and transparency, and tubes were measured for transparency, anti-kinking properties, restoration capability after occlusion and heat resistance, by the following methods.

(Styrene Content)

Calculated on the basis of mass of each monomer used for polymerization.

(Number Average Molecular Weight)

A number average molecular weight (Mn) as polystyrene was determined by GPC measurement.

(Vinyl Bond Content)

A block copolymer before hydrogenation was dissolved in deuterated chloroform ($CDCl_3$) and measured for $^1$H-NMR spectrum, and a vinyl bond content was calculated on the basis of sizes of peaks corresponding to 1,2-bonds and 3,4-bonds.

(Hydrogenation ratio)

Hydrogenation ratio was calculated on the measurement of iodine numbers of the block copolymer before and after hydrogenation.

TABLE 2

|  |  | Example 1 | Example 2 | Example 3 |
|---|---|---|---|---|
| Amount ratio (%) | Layer (I) | (a) PP F327 20% (b) KratonGG1 652 80% | (a) PP F327 20% (b) Hybrar HVS-3 80% | (a) PP F327 20% (b) DYNARON 1320P 80% |
|  | Layer (II) | (a) PP F327 50% (b) KratonGG1 652 50% | (a) PP F327 50% (b) Hybrar HVS-3 50% | (a) PP F327 50% (b) DYNARON 1320P 50% |
| Thickness ratio | Layer (I) | 940 | 940 | 940 |
|  | Layer (II) | 30 × 2 | 30 × 2 | 30 × 2 |
| Sticking during srerilization |  | 3~3.4 | 3~3.4 | 3~3.5 |
| Radius when kinking occurred |  | 17 mm | 17 mm | 16 mm |
| Solvent bonding properties |  | 90~120 N | 90~120 N | 90~110 N |

|  |  | Example 4 | Example 5 | Comparative Example 1 |
|---|---|---|---|---|
| Amount ratio (%) | Layer (I) | (a) PP F327 20% (b) Hybrar HVS-3 80% | (a) PP F327 20% (b) Kraton-GG1652 80% | (a) PP F327 20% (b) Hybrar HVS-3 80% |
|  | Layer (II) | (c) PP F327 50% (d) Hybrar HVS-3 50% | (a) PP F327 100% | (a) PP F327 40% (b) Hybrar HVS-3 60% |
| Thickness ratio | Layer (I) | 800 | 940 | 940 |
|  | Layer (II) | 100 × 2 | 30 × 2 | 30 × 2 |
| Sticking during sterilization |  | 3~3.4 | No sticking | 3.4~3.8 |
| Radius when kinking occurred |  | 23 mm | 37 mm | 17 mm |
| Solvent bonding properties |  | 90~110 N | Less than 10 N | 90~110 N |

(Flexibility of Resin Composition)

A test piece having a length of 30 mm, a width of 5 mm and a thickness of 1 mm was prepared, and measured for a dynamic viscoelasticity dependent upon temperatures. The elastic modulus at 25° C. was employed. Measurement conditions were as follows. Tensile mode (sine wave distortion, amplitude displacement; 10 μm, frequency; 1 Hz), a chuck—chuck distance; 20 mm, measurement temperature range; −100–150° C., a temperature elevation rate; 3° C./minute (Transparency of Resin Composition)

A sheet having a thickness of 1 mm was prepared, and measured for a haze value with a haze meter according to a method defined in JIS K7105, and the haze value was used as an index for transparency of a resin composition.

(Transparency of Tube)

When a tube was filled with water, a degree to which air bubbles inside the tube were visually observed was used as an index for transparency.

(Anti-Kinking Properties of Tube)

A tube having a length of 20 cm was bent in the form of a U-letter and left as it was for approximately 1 minute, and then the tube was observed for a kinking. The tube was measured for a radius of curvature with an R gage, and a smallest radius of curvature at which no kinking occurred was used as an index for anti-kinking properties.

(Restoration Capability of Tube after Occlusion)

A tube filled with a saline solution was closed with a medical tube forceps for 15 hours, and then the forceps was removed. A time period was measured before the tube formed a through passage inside and used as an index for restoration capability of tube after occlusion.

(Resistance Against Tube/Tube Sticking Under Heat)

Two tubes having a length of 10 cm each were stacked such that 5 cm each of them were stacked one on the other in parallel, and the stacked portions were bound with a paper tape. The tubes were subjected to autoclave sterilization (121° C., 20 minutes), and the binding paper tape was removed. The tubes were measured for a shear peel strength, and the tube/tube sticking strength was used as an index for resistance against sticking under heat. As a shear peel strength, a maximum value obtained under conditions of a test speed of 100 mm/minute with a tensile tester was employed.

(Resistance Against Tube/Film Sticking Under Heat)

A tube having a length of 10 cm was placed in a sterilization bag (supplied by Hogy Medical Co.) and subjected to autoclave sterilization (121° C., 20 minutes). Then, the film was measured for a 180° peel strength, and By the tube/film sticking was used as an index for resistance against sticking under heat. As a shear peel strength, an average value obtained under conditions of a test speed of 100 mm/minute with a tensile tester was employed.

Referential Example 2

Preparation of Copolymer No. 1

In a pressure vessel where dry nitrogen had been substituted, styrene was polymerized at 60° C. in cyclohexane as a solvent in the presence of s-butyllithium as a polymerization initiator, and then TMEDA was added as a Lewis base. Then, isoprene and styrene were consecutively polymerized to give a styrene-isoprene-styrene block copolymer. The thus-obtained block copolymer was hydrogenated in cyclohexane in the presence of Pd/C as a catalyst under a 2 MPa hydrogen atmosphere, to give a hydrogenated block copolymer (the hydrogenated block copolymer obtained in Referential Example 2 will be abbreviated as "Copolymer No. 1" hereinafter). Table 3 shows a styrene content, a number average molecular weight, a vinyl bond content and a hydrogenation ratio of the obtained Copolymer No. 1.

Referential Example 3

Preparation of Copolymer No. 2

Styrene, a mixture of isoprene with butadiene [isoprene/butadiene=60/40 (mass ratio)] and styrene were consecutively polymerized in a cyclohexane solvent in the presence of s-butyllithium and TMEDA in the same manner as in Referential Example 2, to give a styrene-(isoprene/butadiene)-styrene block copolymer. The thus-obtained block copolymer was hydrogenated in the same manner as in Referential Example 2, to give a hydrogenated block copolymer (the hydrogenated block copolymer obtained in Referential Example 3 will be abbreviated as "Copolymer No. 2" hereinafter). Table 3 shows a styrene content, a number average molecular weight, a vinyl bond content and a hydrogenation ratio of the obtained Copolymer No. 2.

Referential Example 4

Preparation of Copolymer No. 3

Styrene, butadiene and styrene were consecutively polymerized in a cyclohexane solvent in the presence of s-butyllithium and TMEDA in the same manner as in Referential Example 2, to give a styrene-butadiene-styrene block copolymer. The thus-obtained block copolymer was hydrogenated in the same manner as in Referential Example 2, to give a hydrogenated block Copolymer No. 3 (the hydrogenated block copolymer obtained in Referential Example 4 will be abbreviated as "Copolymer No. 3" hereinafter). Table 3 shows a styrene content, a number average molecular weight, a vinyl bond content and a hydrogenation ratio of the obtained Copolymer No. 3.

TABLE 3

| Co-polymer No. | Molecular structure before hydrogenation (Note) | Styrene content (%) | Number average molecular weight (× 10⁴) | Vinyl bond content (mol %) | Hydrogenation ratio (%) |
|---|---|---|---|---|---|
| REx. 2 | 1 | A-B-A | 20 | 10.3 | 55 | 80 |
| REx. 3 | 2 | A-C-A | 20 | 10.8 | 60 | 82 |
| REx. 4 | 3 | A-D-A | 20 | 10.5 | 72 | 83 |

(Note)
A: Polystyrene block
B: Polyisoprene block
C: Poly(isoprene/butadiene) block
D: Polybutadiene block Examples 6–9 and Comparative Examples 2–3

As a polypropylene resin (a), a commercially available block type polypropylene [BC1B (trade name), supplied by Nippon Polychem.], a random type polypropylene [J215W (trade name), supplied by Grand Polymer Co.] and a homo type polypropylene [MA3 (trade name), supplied by Nippon Polychem.] were used. As a copolymer (b), Copolymer No. 1 obtained in Referential Example 2, Copolymer No. 2 obtained in Referential Example 3, Copolymer No. 3 obtained in Referential Example 4 and a commercially available hydrogenated styrene-butadiene rubber [DYNARON 1320P (trade name), supplied by JSR Co., Ltd] were used.

The polypropylene resin (a) and the copolymer (b) were kneaded in an amount ratio (ratio by mass) shown in Table 4 at 230° C. in a twin-screw extruder, to give resin compositions.

TABLE 4

| | Example 6 | Example 7 | Examle 8 |
|---|---|---|---|
| Layer (I) (Thickness 1 mm) | (a) PP BC1B (5%) (b) Copolymer No. 1 (95%) | (a) PP J215W (40%) (b) Copolymer No. 2 (60%) | (a) PP J215W (20%) (b) Copolymer No. 3 (80%) |
| Layer (II), inner layer (Thickness, 30 μm) | (a) PP BC1B (90%) (b) Copolymer No. 1 (10%) | None | None |
| Layer (II), outer layer (Thickness, 30 μm) | None | (a) PP J215W (80%) (b) Copolymer No. 2 (20%) | (a) PP J215W (50%) (b) Copolymer No. 3 (50%) |
| Flexibility of tube*¹ | ⊚ | ○ | ⊚ |
| Elastic modulus of layer (I) | 8.5 MPa | 50 MPa | 11 MPa |
| Transparancy of tube*² | ○ | ○ | ○ |
| Haze of layer (I) (%) | 2% | 5% | 4% |
| Haze of layer (II) (%) | 20% | 16% | 7% |
| Anti-kinking properties*³ | ○ 12 mm | ○ 12 mm | ○ 11 mm |
| Remarks | None | None | None |

| | Example 9 | Comparative example 2 | Comparataive example 3 |
|---|---|---|---|
| Layer (I) (Thickness 1 mm) | (a) PP MA3 (30%) (b) DYNARON 1320P (70%) | (a) PP BC1B (3%) (b) Copolymer No. 1 (97%) | (a) PP J215W (50%) (b) Copolymer No. 2 (50%) |
| Layer (II), inner layer (Thickness 30 μm) | None | (a) PP BC1B (90%) (b) Copolymer No. 1 (10%) | None |
| Layer (II), outer layer (Thickness 30 μm) | (a) PP MA3 (100%) | None | (a) PP J215W (80%) (b) Copolymer No. 2 (20%) |
| Flexibility of tube*¹ | ⊚ | ⊚ | x |
| Elastic modulus of layer (I) | 15 MPa | 8 MPa | 100 MPa |
| Transparancy of tube*² | ○ | ○ | ○ |
| Haze of layer (I) (%) | 4% | 1% | 7% |
| Haze of layer (II) (%) | 25% | 20% | 16% |
| Anti-kinking properties*³ | ○ 13 mm | ○ 12 mm | ○ 15 mm |
| Remarks | None | Cross section of tube deformed to oval | deficient in flexibility |

(Notes)
*¹Evaluation of flexibility of tube was based on elastic modulus of layer (I); ⊚: less than 30 MPa, ○: 30–100 MPa, x: over 100 MPa
*²Evaluation base of transparency of tube: ○ Air bubbles were recognizable, x: No air bubble was recognizable.
*³Evaluation of anti-kinking properties of tube was based on maximum diameter at which kinking occurred; ○: less than 20 mm, x: over 20 mm The obtained resin compositions were formed at 230° C. into a dual layer tube having an outer diameter of 5.6 mm and an inner diameter of 3.3 mm, and the dual tube was evaluated for flexibility, transparency, anti-kinking properties, resistance against sticking under heat and restoration capability after occlusion. Table 4 shows the results.

It is seen from Table 4 that the multi-layered tubes of Examples 6 to 9 are excellent in flexibility, transparency and anti-kinking properties, but that when the amount ratio of the polypropylene resin in the layer (I) is small like Comparative Example 2, it is difficult to form a tube and the cross section of the tube is deformed. Further, when the a) amount ratio of the polypropylene resin in the layer (I) is large like Comparative Example 3, the flexibility of the tube is deficient.

Examples 10–13

A commercially available random type polypropylene [J215W (trade name), supplied by Grand Polymer Co.] was used as a polypropylene resin (a), and copolymer No. 1 obtained in Referential Example 2 was used as a copolymer (b).

The above polypropylene resin (a) and the copolymer (b) were kneaded in an amount ratio (ratio by mass) shown in Table 5 at 230° C. in a twin-screw extruder, to give a resin composition. The obtained resin compositions were formed at 230° C. into a three-layered tube having an outer diameter of 5.6 mm and an inner diameter of 3.3 mm as shown in FIG. 1(3), and the three-layered tube was evaluated for flexibility, transparency, anti-kinking properties, resistance against sticking under heat and restoration capability after occlusion. Table 5 shows the results. It is seen from Table 5 that the multi-layered tubes in Examples 10 to 13 are excellent in flexibility, transparency, anti-kinking properties, resistance against sticking under heat and restoration capability after occlusion.

Example 14

A dual layered tube having an outer diameter of 8 mm and an inner diameter of 6 mm was prepared in the same manner as in Example 8, and a three-layered tube having an outer diameter of 6 mm and an inner diameter of 4 mm was prepared in the same manner as in Example 10. These tubes were connected by solvent bonding using tetrahydrofuran. The bonded portion had a tensile bonding strength of 130 N, or attained strong connection.

Example 15

The three-layered tube prepared in Example 10 was used to obtain a blood circuit for dialysis. The three-layered tube was strongly connected to a connector. A three-layered tube portion of the blood circuit was closed with a medical tube forceps for 15 hours, and then the forceps was removed. The tube formed a through passage inside within 3 seconds after the removal. The above three-layered tube is excellent in flexibility, transparency, anti-kinking properties, restoration capability after occlusion and resistance against sticking under heat, and it is shown that it is at a practical level when it is used in a medical device or a medical tube, particularly, a circuit for extracorporeal circulation.

Comparative Example 4

A commercially available polypropylene [F327 (trade name), supplied by Grand Polymer Co.] was used as a polypropylene resin (a), Copolymer No. 1 obtained in Referential Example 2 was used as a copolymer (b), and these were used for a layer (I) (intermediate layer) and a layer (II) as an outer layer. A high-density polyethylene [HJ490 (trade name), supplied by Japan Polychem Co.] was used for a layer (II) as an inner layer. And, a three-layered tube having a constitution shown in Table 6 was prepared. When the three-layered tube was closed with a forceps for 15 hours after sterilization with high-pressure steam, the time period before the formation of a through passage was 120 seconds or longer.

TABLE 5

|  | Table 10 | Table 11 | Table 12 | Table 13 |
|---|---|---|---|---|
| Layer (I) (Thickness 1 mm) | (a) PP J215W (20%) (b) Copolymer No. 1 (80%) | (a) PP J215W (20%) (b) Copolymer No. 1 (80%) | (a) PP J215W (20%) (b) Copolymer No. 1 (80%) | (a) PP J215W (20%) (b) Copolymer No. 1 (80%) |
| Layer (II), inner layer (Thickness 30 μm) | (a) PP J215W (60%) (b) Copolymer No. 1 (40%) | (a) PP J215W (60%) (b) Copolymer No. 1 (40%) | (a) PP J215W (40%) (b) Copolymer No. 1 (60%) | (a) PP J215W (100%) |
| Layer (II'), outer layer (Thickness 30 μm) | (a) PP J215W (50%) (b) Copolymer No. 1 (50%) | (a) PP J215W (40%) (b) Copolymer No. 1 (60%) | (a) PP J215W (70%) (b) Copolymer No. 1 (30%) | (a) PP J215W (60%) (b) Copolymer No. 1 (40%) |
| Flexibility of tube*1 | ⊚ | ⊚ | ⊚ | ⊚ |
| Elastic modulfs of layer (I) | 12 MPa | 12 MPa | 12 MPa | 12 MPa |
| Transparendy of tube*2 | o | o | o | o |
| Haze of layer (I) (%) | 3% | 3% | 3% | 3% |
| Haze of layer (II) (%) | 11% | 11% | 5% | 25% |
| Haze of layer (II') (%) | 7% | 5% | 14% | 11% |
| Anti-kinking properties*3 | o 12 mm | o 11 mm | o 15 mm | o 13 mm |
| Resistance against sticking under heat*4 | ⊚ | o | ⊚ | ⊚ |
| Shear peel strength Tube/tube | 34 N | 37 N | 14 N | 20 N |
| 180° Peel strengh Tube/film | 2 N | 10 N | 1 N | 2 N |
| Restoration capability after occlusion*5 | o 3 seconds | o 3 seconds | o 15 seconds | ⊚ 2 seconds |
| Remauks | None | None | None | None |

(Notes)
*1Evaluation of flexibility of tube was based on elastic modulus of layer (I); ⊚: less than 30 MPa, o: 30–100 MPa, x: over 100 MPa
*2Evaluation base of transparency of tube: o Air bubbles were recognizable, x: No air bubble was recognizable.
*3Evaluation of anti-kinking properties of tube was based on maximum diameter at which kinking occurred; o: less than 20 mm, x: 20 mm or more
*4Evaluation of resistance against sticking under heat was based on shear peel strength of tube/tube sticking; ⊚: less than 35 N, o: 35–40 N, x: over 40 N and also based on 180° peel strength; o: less than 1.0 N, x: 10 N or more
*5Evaluation of restoration capability after occlusion was based on time period for which through passage was formed; ⊚: less than 3 seconds, o: 3–120 seconds, x: over 120 seconds

TABLE 6

|  | Comparative Example 4 |
| --- | --- |
| Layer (I) | (a) PP F327 (30%) |
| (thickness 1 mm) | (b) copolymer No. 1 (70%) |
| Layer (II), inner layer | High-density polyethylene |
| (thickness 30 μm) | HJ490 |
| Layer (II), outer layer | (a) PP F327 (50%) |
| (thickness 30 μm) | (b) copolymer No. 1 (50%) |

INDUSTRIAL UTILITY

According to the present invention, there is provided a multi-layered tube that is excellent in flexibility, transparency, anti-kinking properties, restoration capability after occlusion, heat resistance, resistance against sticking under heat and bonding properties, and which is free from elution of a plasticizer and generates no toxic gas when incinerated.

The multi-layered tube of the present invention can be used as it is or can be used as a component of medical devices such as a blood tube, a blood bag, an medical solution bag, an infusion tube, a blood circuit, a catheter, etc., and particularly for a circuit for extracorporeal circulation. Further, it is not limited to medical applications, but can be applied to various fields such as industrial fields and fields of general household articles.

What is claimed is:

1. A tube consisting of an inner, intermediate and outer resin layer, wherein the inner and outer layers are made of resin (II) and the intermediate layer is formed of resin (I), wherein
   resin (I) comprises:
      (a) 5 to 40 mass % of a polypropylene resin and
      (b) 95 to 60 mass % of at least one hydrogenated copolymer selected from the group consisting of:
         (i) a first hydrogenated block copolymer comprising a hydrogenated block copolymer formed of (A) a polymer block from a vinyl aromatic compound and (B) an isoprene polymer block, and the isoprene polymer block (B) having a 1,2-bond and 3,4-bond content of 10 to 75 mol %,
         (ii) a second hydrogenated block copolymer comprising a hydrogenated block copolymer formed of said (A) polymer block from a vinyl aromatic compound and (C) a polymer block from isoprene and butadiene, and the polymer block (C) having a 1,2-bond and a 3,4-bond content of 20 to 85 mol %,
         (iii) a third hydrogenated block copolymer comprising a hydrogenated block copolymer formed of said (A) polymer block from a vinyl aromatic compound and a butadiene polymer block, and the polymer block (D) having a 1,2-bond content of at least 30 mol %, and
   resin (II) comprises:
      (a') 45 to 100 mass % of a polypropylene resin and
      (b') 55 to 0 mass % of the above at least one hydrogenated copolymer,
   wherein resin (II), which forms the outer layer contains 45 to 70 mass % of the polypropylene resin and 55 to 30 mass % of the at least one hydrogenated copolymer,
   wherein resins (I) and (II) do not contain random copolymer,
   wherein said tube has (i) a tube/tube a shear peel strength of less than 35 N, as measured on a stuck or adhered portion of the outermost layer of one said tube against the outermost layer of another said tube after autoclave sterilization at 121° C. for 20 minutes, and has (ii) a tube/film 180° peel strength of less than 10 N, as measured on a stuck or adhered portion of the outermost layer of said tube and an innermost polypropylene layer of a sterilization bag, by the test method defined in JIS K6854 after autoclave sterilization at 121° C. for 20 minutes,
   wherein said resin (I) forms a thick substrate layer and resin (II) forms a connection layer thinner than the substrate layer, the connection layer being capable of connecting to another tube or article by hot melt bonding, solvent bonding or adhesive bonding,
   wherein said tube can form an arc having a radius of 20 mm without kinking,
   thereby the tube showing good resistance against tube/tube sticking and tube/film sticking after high-pressure steam sterilization.

2. The tube of claim 1, wherein said resin (II), which forms the inner layer, contains 70 to 100 mass % of the polypropylene resin and 30 to 0 mass % of the at least one hydrogenated copolymer.

3. The tube of claim 1, wherein the tube has an outer layer/intermediate layer/inner layer thickness ratio of 20–30/940–960/20∝30.

4. The tube of claim 1, wherein said first hydrogenated block copolymer has a vinyl aromatic compound component content of 10 to 40 mass %, and at least 70% of carbon—carbon double bonds of the isoprene polymer block (B) of the first block copolymer are hydrogenated.

5. The tube of claim 1, wherein said second hydrogenated block copolymer has a vinyl aromatic compound component content of 10 to 40 mass %, the polymer block (C) has an isoprene component/butadiene component weight ratio of 5/95 to 95/5 and at least 70% of carbon—carbon double bonds of the polymer block (C) of the second block copolymer are hydrogenated.

6. The tube of claim 1, wherein said third hydrogenated block copolymer has a vinyl aromatic compound component content of 10 to 40 mass %, and at least 70% of carbon—carbon double bonds of the butadiene polymer block (D) of the third block copolymer are hydrogenated.

7. The tube of claim 1, wherein the hydrogenated copolymer of resin (I) is a first hydrogenated block copolymer obtained by hydrogenating a block copolymer formed of said (A) polymer block from a vinyl aromatic compound and said (B) isoprene polymer block.

8. The tube of claim 1, wherein the hydrogenated copolymer of resin (I) is a second hydrogenated block copolymer obtained by hydrogenating a block copolymer formed of said (A) polymer block from a vinyl aromatic compound and said (C) polymer block from isoprene and butadiene.

9. The tube of claim 1, wherein the hydrogenated copolymer of resin (I) is a third hydrogenated block copolymer obtained by hydrogenating a block copolymer formed of said (A) polymer block from a vinyl aromatic compound and said (D) butadiene polymer block.

10. The tube of claim 1, wherein the hydrogenated copolymer of resin (II) is a first hydrogenated block copolymer obtained by hydrogenating a block copolymer formed of said (A) polymer block from a vinyl aromatic compound and said (B) isoprene polymer block.

11. The tube of claim 1, wherein the hydrogenated copolymer of resin (II) is a second hydrogenated block copolymer obtained by hydrogenating a block copolymer formed of said (A) polymer block from a vinyl aromatic compound and (C) a polymer block from isoprene and butadiene.

12. The tube of claim 1, wherein the hydrogenated copolymer of resin (II) is a third hydrogenated block copolymer obtained by hydrogenating a block copolymer formed of said (A) polymer block from a vinyl aromatic compound and said (D) butadiene polymer block.

13. The tube of claim 1, wherein said vinyl aromatic compound is styrene.

14. The tube of claim 1, wherein the polypropylene resin in resin (I) has a bending flexural modulus of 200 to 400 MPa and the polypropylene resin in resin (II) has a flexural modulus of 500 to 900 MPa.

15. The tube of claim 1 that has been sterilized.

16. A medical device comprising the tube of claim 1 connected to at least one other member.

17. The medical device of claim 16, wherein said one other member is selected from the group consisting of a blood tube, an infusion tube, a catheter, and a balloon catheter.

18. A circuit for extracorporeal circulation comprising the tube of claim 1.

* * * * *